United States Patent [19]

Hoffmann

[11] Patent Number: 4,556,065
[45] Date of Patent: Dec. 3, 1985

[54] ELECTRODE STRUCTURE FOR ELECTRIC CONTACTOR

[75] Inventor: Heiner Hoffmann, Wippingen, Fed. Rep. of Germany

[73] Assignee: Ingeborg Niess Elektromedizinischee Apparate, Blaustein-Herringen, Fed. Rep. of Germany

[21] Appl. No.: 570,009

[22] Filed: Jan. 11, 1984

[30] Foreign Application Priority Data

Jan. 12, 1983 [DE] Fed. Rep. of Germany ....... 3300765

[51] Int. Cl.⁴ .............................................. H61B 5/04
[52] U.S. Cl. ..................................... 128/639; 128/643
[58] Field of Search ............... 128/639, 640, 641, 643, 128/644, 802

[56] References Cited

U.S. PATENT DOCUMENTS

| | | | |
|---|---|---|---|
| 3,640,270 | 2/1972 | Hoffmann | 128/2.1 E |
| 4,166,453 | 9/1979 | McClelland | 128/803 |
| 4,248,243 | 2/1981 | Niess et al. | 128/696 |
| 4,270,543 | 6/1981 | Tabuchi et al. | 128/640 |
| 4,273,135 | 6/1981 | Larimore et al. | 128/802 |

FOREIGN PATENT DOCUMENTS 1939523 10/1972 Fed. Rep. of Germany .
2925909 11/1981 Fed. Rep. of Germany .

Primary Examiner—Kyle L. Howell
Assistant Examiner—David Shay
Attorney, Agent, or Firm—Karl F. Ross; Herbert Dubno

[57] ABSTRACT

A contactor for diagnostic or therapeutic purposes has a nonmetallic suction cup surrounding a recessed electrode which comprises a contact plate of compressed or sintered silver powder admixed with a silver salt, e.g. silver chloride, supported on a conductive body of graphite. A metallic tube traversed by an airstream, communicating through a lateral orifice with the interior of the suction cup, passes through a bore of the graphite body to form part of a conductive connection between the electrode and a remote voltage source. The tube is silver-coated in its area of contact with the graphite body, as is a grub screw holding that tube in position within that body.

1 Claim, 1 Drawing Figure

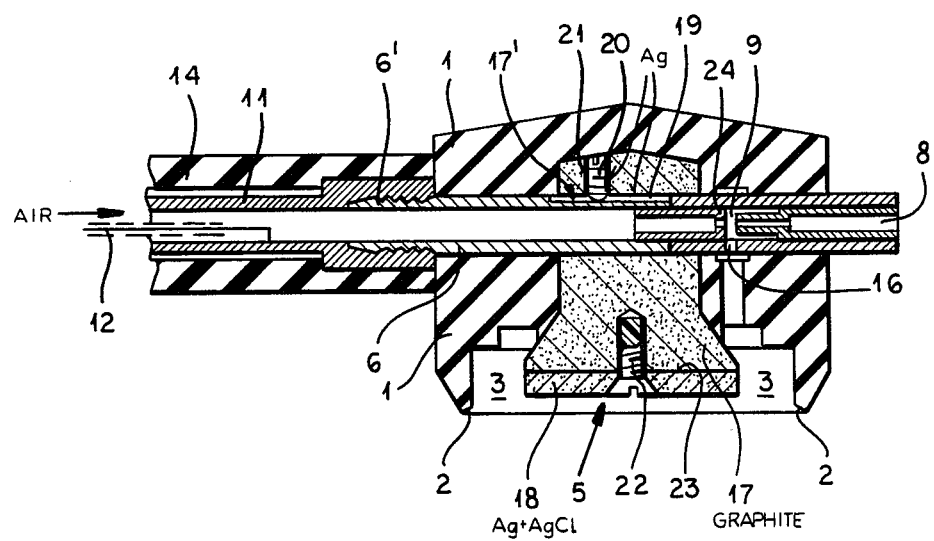

ELECTRODE STRUCTURE FOR ELECTRIC CONTACTOR

FIELD OF THE INVENTION

My present invention relates to a contactor for diagnostic or therapeutic purposes, designed for establishing electric communication between organic tissue—such as the skin of a human or animal body—and an external circuit of an associated instrument.

BACKGROUND OF THE INVENTION

A contactor of this character is the subject matter of my commonly owned prior U.S. Pat. No. 3,640,270. As disclosed in that prior patent, the contactor has a generally cup-shaped housing of nonmetallic material with a mouth bounded by a tissue-engaging rim; the housing contains an electrode which is recessed within the rim but accessible by way of its mouth so as to be able to make contact with the skin of a person or animal to be tested or treated. The mouth of the cup communicates with a low-pressure zone inside a conduit which is traversed by a flow of high-pressure gas, generally air, and is embedded in the elastomeric material of the housing. The low-pressure zone lies at the outlet of a Venturi nozzle accelerating the flow of gas which is discharged into the atmosphere at an open end of the conduit. The latter includes a metal tube which also forms part of a conductive connection between the external conduit, which may include a voltage source, and the electrode.

The electrode of the contactor described in that prior patent comprises a metallic plate carrying a sponge which is permeated by a liquid electrolyte and has an exposed skin-engaging surface. Another type of electrode suitable for such a device, described in commonly owned German Pat. No. 25 29 909, is a plate of coherent particles—sintered or simply pressed—of a mixture of silver and one or more silver salts such as silver chloride, silver bromide, silver iodide, silver rhodanide or silver cyanide. Such an electrode, which has the advantage of low contact resistance, must be protected from interaction with adjoining elements of different metallic materials which can give rise to detrimental local currents. It is for this reason that, as taught in the German patent referred to, a contact plate consisting of the aforedescribed compacted mixture of metallic silver and a silver salt is supported on a metallic body coated with silver at least in its area adjoining the plate. That German patent also shows a retaining screw which holds the contact plate onto the supporting body and consists at least on an outer surface of nonconductive material; a titanium screw, with an oxide layer on its surface, is particularly mentioned in this context. An electrode of this type, comprising a massive metallic supporting body made at least partly of silver, is relatively expensive.

Reference may also be made to another commonly assigned earlier U.S. patent of mine, No. 4,248,243, showing a contactor of the type here envisaged connected to a diagnostic apparatus such as an electrocardiograph.

OBJECTS OF THE INVENTION

The general object of my present invention is to provide an improved electrode structure for such a contactor which is less expensive than that known from the German patent but retains the advantages of low contact resistance and avoidance of local voltage differences giving rise to destructive currents.

A more particular object is to provide means in the contactor for conveniently connecting such an electrode to an external circuit with the aid of a metallic tube as known per se from my first-mentioned U.S. patent.

SUMMARY OF THE INVENTION

In accordance with the present improvement, the electrode of the contactor comprises a contact plate of the aforedescribed type—consisting of coherent particles of a mixture of silver and a silver salt—supported on a body of solid graphite which is partly embedded in the nonmetallic housing while being in galvanic contact with conductor means inside the housing extending to the external circuit.

Pursuant to a more particular feature of my invention, the graphite body has a bore which is traversed by a metallic tube carrying the flow of air or other high-pressure gas and serving to connect that body to the external circuit. The tube preferably is made of ferrous metal such as steel having a silver coating at least in its area of conductive contact with the graphite body.

Advantageously, the tube is secured to the graphite body by a grub screw which penetrates part of that body and also has a silver coating in its area of contact therewith.

BRIEF DESCRIPTION OF THE DRAWING

The above and other features of my invention will now be described in detail in reference to the accompanying drawing the sole FIGURE of which shows, in axial section, a contactor provided with my improved electrode structure.

SPECIFIC DESCRIPTION

In the drawing, in which many of the reference numerals correspond to those used for similar elements in my prior U.S. Pat. No. 3,640,270, I have shown a cup-shaped housing 1 of rubber or similar elastomeric material with a rim 2 defining a mouth 3 in which an electrode 5 is recessed. This electrode comprises a contact plate 18 of sintered particles of silver and a silver salt, preferably silver chloride. The surface 23 of plate 18 rests against a body 17 of solid graphite to which it is attached by a screw 22 with a tapered, countersunk head threaded directly into that body.

A steel tube 6 conducts air under pressure from a nonillustrated source to an outlet end 8 opening into the atmosphere, this tube being internally provided with a Venturi nozzle forming a constriction 24 beyond which a low-pressure zone 9 communicates via a lateral orifice 16 with mouth 3. Any contact liquid spread on the exposed surface of electrode plate 18 and aspirated into the tube 6 is discharged through outlet 8.

A threaded end 6' of tube 6 is attached to a metallic nipple 11 designed to retain a flexible hose 14 through which the air under pressure is admitted to the tube. An insulated wire 12 attached to nipple 11 forms part of the electrical connection between electrode 5 and the external circuit.

Tube 6 passes through a transverse bore 19 of graphite body 17 and is provided, in its area of contact with that body, with an outer coating of silver so as to equalize the surface potentials existing across the graphite. For the same purpose a grub screw 20, threaded into a lateral bore 21 of body 17 and extending into a keyway 17' of tube 6, is also provided with a silver coating. The mounting screw 22 may consist entirely of plastic material, as indicated, but can also be made of titanium as known from the above-identified German patent.

I have found that the described contactor, with its electrode 5 including a graphite-supported silver plate, can detect bioelectric contact potentials of low magnitude on human or animal skins which are to be transmitted to the associated apparatus in a case where no voltages are to be applied from the apparatus to the skin of the patient.

I claim:

1. A contactor for establishing electric communication with organic tissues comprising:

a nonmetallic cup-shaped housing with a mouth bounded by a tissue-engaging rim;

an electrode in said housing comprising a contact plate of coherent particles of a mixture of silver and silver salt recessed within said rim, said contact plate having an exposed surface accessible through said mouth, a body of solid graphite having an elongated portion received in said housing and an end portion wider than said elongated portion and integral therewith disposed in said mouth and abutting said plate, and a screw traversing said plate and threaded into said end portion for retaining said plate on said end portion, said elongated portion being formed with a transverse bore;

a metallic tube extending through said body and through said bore forming a contactor in conductive contact with said body and communicating with a source of high-pressure gas;

means communicating with said tube forming a Venturi nozzle establishing a reduced pressure zone communicating with said mouth and opening into the atmosphere; and a further screw threaded into said body and bracing said tube in conductive contact with said body, said tube consisting of a ferrous metal having a silver coating at least in an area of conductive contact between said tube and said body, said further screw having a silver coating where it contacts said body.

* * * * *